US009562226B2

(12) United States Patent
Cramer et al.

(10) Patent No.: US 9,562,226 B2
(45) Date of Patent: Feb. 7, 2017

(54) DEVICE FOR ISOLATING AN ANALYTE FROM A SAMPLE, AND METHODS OF USE

(71) Applicants: Quidel Corporation, San Diego, CA (US); Northwestern University, Evanston, IL (US)

(72) Inventors: Ashley Danielle Cramer, East Stroudsburg, PA (US); Mark J. Fisher, Highland Park, IL (US); Jacqueline R. Groves, Chicago, IL (US); David M. Kelso, Wilmette, IL (US); Lawrence W. Markus, Mundelein, IL (US); Zaheer Parpia, Evanston, IL (US); Kunal Sur, Evanston, IL (US); Tom Westberg, Gurnee, IL (US)

(73) Assignees: Quidel Corporation, San Diego, CA (US); Northwestern University, Evanston, IL (US)

( * ) Notice: Subject to any disclaimer, the term of this patent is extended or adjusted under 35 U.S.C. 154(b) by 0 days.

(21) Appl. No.: 13/889,079

(22) Filed: May 7, 2013

(65) Prior Publication Data

US 2013/0302791 A1    Nov. 14, 2013

Related U.S. Application Data

(60) Provisional application No. 61/644,390, filed on May 8, 2012, provisional application No. 61/776,626, filed on Mar. 11, 2013.

(51) Int. Cl.
*B01L 3/00* (2006.01)
*C12N 15/10* (2006.01)
*G01N 35/00* (2006.01)

(52) U.S. Cl.
CPC .......... *C12N 15/1013* (2013.01); *B01L 3/502* (2013.01); *B01L 3/502761* (2013.01); *B01L 2200/0631* (2013.01); *B01L 2200/0647* (2013.01); *B01L 2200/0668* (2013.01); *B01L 2200/0673* (2013.01); *B01L 2300/0809* (2013.01);
(Continued)

(58) Field of Classification Search
None
See application file for complete search history.

(56) References Cited

U.S. PATENT DOCUMENTS 4,921,612 A    5/1990  Sirkar
5,230,866 A *  7/1993  Shartle ............. B01L 3/502723
                                                       422/68.1
(Continued)

FOREIGN PATENT DOCUMENTS

DE    102009035941 A1    2/2011
EP          1707965 A1    4/2006
(Continued)

OTHER PUBLICATIONS

JP2003290682 description english translation.*
(Continued)

*Primary Examiner* — Betty Forman
(74) *Attorney, Agent, or Firm* — Jacqueline F. Mahoney; Judy M. Mohr; McDermott Will & Emery LLP

(57) ABSTRACT

A device for extraction or isolation of an analyte, such as a nucleic acid, a protein, or a cell, from a sample, and in particular from a biological sample is described. Methods of using the device are also described.

15 Claims, 4 Drawing Sheets

(52) U.S. Cl.
CPC . *B01L 2300/0861* (2013.01); *B01L 2400/043* (2013.01); *G01N 35/0098* (2013.01)

(56) References Cited

U.S. PATENT DOCUMENTS

| | | | |
|---|---|---|---|
| 5,238,810 | A | 8/1993 | Fujiwara et al. |
| 5,279,936 | A | 1/1994 | Vorpahl |
| 5,466,575 | A | 11/1995 | Cozzette et al. |
| 6,040,193 | A | 3/2000 | Winkler et al. |
| 6,989,237 | B2 | 1/2006 | Fulwyler et al. |
| 7,354,750 | B2 | 4/2008 | Simpson et al. |
| 7,745,129 | B1 | 6/2010 | Schatz |
| 7,820,454 | B2 | 10/2010 | Su et al. |
| 8,187,808 | B2 | 5/2012 | Kelso et al. |
| 8,206,918 | B2 | 6/2012 | Kelso et al. |
| 2001/0029810 | A1 | 10/2001 | Ho |
| 2002/0151040 | A1 | 10/2002 | O'Keefe et al. |
| 2004/0011650 | A1* | 1/2004 | Zenhausern ...... B01L 3/502746 204/547 |
| 2005/0191759 | A1 | 9/2005 | Pedersen-Bjergaard et al. |
| 2005/0202504 | A1 | 9/2005 | Anderson et al. |
| 2005/0266429 | A1 | 12/2005 | Kleiber et al. |
| 2006/0134793 | A1 | 6/2006 | Key |
| 2007/0036679 | A1 | 2/2007 | Munenaka |
| 2007/0184463 | A1 | 8/2007 | Molho et al. |
| 2008/0160639 | A1 | 7/2008 | Su et al. |
| 2008/0217246 | A1 | 9/2008 | Benn et al. |
| 2008/0226500 | A1 | 9/2008 | Shikida et al. |
| 2008/0254467 | A1 | 10/2008 | Regan |
| 2008/0277348 | A1 | 11/2008 | Izumizawa |
| 2009/0220948 | A1* | 9/2009 | Oviso et al. ........................ 435/6 |
| 2009/0246782 | A1 | 10/2009 | Kelso et al. |
| 2009/0289213 | A1 | 11/2009 | Pipper et al. |
| 2009/0323069 | A1* | 12/2009 | Naessens et al. ............. 356/440 |
| 2010/0120083 | A1 | 5/2010 | Ritzen et al. |
| 2010/0273142 | A1 | 10/2010 | Prins et al. |
| 2010/0291666 | A1 | 11/2010 | Collier et al. |
| 2011/0212509 | A1 | 9/2011 | Beebe et al. |
| 2011/0213133 | A1 | 9/2011 | Beebe et al. |
| 2012/0107811 | A1 | 5/2012 | Kelso et al. |
| 2013/0158240 | A1 | 6/2013 | Beebe et al. |

FOREIGN PATENT DOCUMENTS

| | | | |
|---|---|---|---|
| EP | 2353721 | A2 | 8/2011 |
| FR | 2858688 | A1 | 2/2005 |
| JP | 2003-290682 | A | 10/2003 |
| KR | 1020020021810 | A | 3/2002 |
| WO | WO 2005/069015 | A1 | 7/2005 |
| WO | WO 2005/108620 | A2 | 11/2005 |
| WO | WO 2006/071770 | A2 | 7/2006 |
| WO | WO 2007/102785 | A1 | 9/2007 |
| WO | WO 2009/105711 | A1 | 8/2009 |
| WO | WO 2009/111316 | A2 | 9/2009 |
| WO | WO 2010/091246 | A2 | 8/2010 |
| WO | WO 2011/015454 | A1 | 2/2011 |
| WO | WO 2011/123064 | A1 | 10/2011 |
| WO | WO 2013/169730 | A1 | 11/2013 |

OTHER PUBLICATIONS

International Search Report from related PCT Patent Application No. PCT/US2013/056055 mailded on Nov. 29, 2013.
Chin et al,, "Communication to the editor on protein solubility in organic solvents", Biotechnology and Bioengineering vol. 44, pp. 140-145 (1994).
Dineva et al., "Sample preparation: a challenge in the development of point-of-care nucleic acid based assays for resource-limited settings", Analyst, vol. 132, pp. 1193-1199 (2007).
Furlani and Ng, "Analytical model of magnetic nanoparticle transport and capture in the microvasculature", Physical Review E73, 061919-1-061919-10, 12 pgs. (2006).
International Search Report from PCT Patent Application No. PCT/US2013/039846 mailed on Aug. 20, 2013.
Liu et al., "Self-contained, fully integrated biochip for sample preparation, polymerase chain reaction amplification and DNA microarray detection", Analytical Chemistry, vol. 76, pp. 1824-1831 (2004).
Mylonakis et al., "Plasma viral load testing in the management of HIV infection", Am. Fam. Physician vol. 63, No. 3, pp. 483-490 (2001).
Pipper et al., "Catching bird flu in a droplet", Nature Medicine, vol. 13, No. 10, pp. 1259-1263 and supplementary information, Fig. 1-5, pp. 1-5 (2007).
Shikida et al., "Development of an enzymatic reaction device using magnetic bead-cluster handling", J. Micromech. Microeng., vol. 16, pp. 1875-1883 (2006).
International Search Report from related PCT Patent Application No. PCT/US2013/039880 mailed on Oct. 25, 2013, application now published as WO2013/169730 on Nov. 14, 2013.

* cited by examiner

DEVICE FOR ISOLATING AN ANALYTE FROM A SAMPLE, AND METHODS OF USE

CROSS-REFERENCE TO RELATED APPLICATIONS

This application claims the benefit of U.S. Provisional Application No. 61/644,390, filed May 8, 2012 and of U.S. Provisional Application No. 61/776,626, filed Mar. 11, 2013, each of which is incorporated herein by reference in its entirety.

TECHNICAL FIELD

The subject matter described herein relates generally to a device useful for extraction or isolation of an analyte, such as a nucleic acid, a protein, or a cell, from a sample, and in particular from a biological sample.

BACKGROUND

Effective analysis of biological entities, such as proteins or nucleic acids, in biological samples generally requires that the target entity in question first be isolated from the biological matrix, which frequently includes a complex mixture of non-target substances. The effective isolation of analytes is a prerequisite for efficient downstream analysis of the analyte, including, for example, amplification of a nucleic acid for detection and quantification. It is also important, in many cases, such as in nucleic acid amplification, that the isolated species not contain residues of certain reagents and/or solvents used during isolation.

Existing methods of isolation frequently involve multi-step processes, often requiring multiple extraction and/or centrifugation steps, which require trained personnel and can introduce risks of contamination and/or loss of sample. A need exists for a self-contained device that is effective to isolate an analyte from a biological sample, such as obtained from a patient, with minimal operator manipulation of sample and reagents.

BRIEF SUMMARY

The following aspects and embodiments thereof described and illustrated below are meant to be exemplary and illustrative, not limiting in scope.

Disclosed herein, in one aspect, is a sample isolation device, the device comprising a rigid body having a first face and a second face, and defining within the first face: a first cavity having an outlet, a second cavity, and a third cavity, a first flow path connecting the first cavity and the second cavity, the first flow path comprising a constricted region between the first cavity and the first flow path, and a second flow path connecting the second cavity and the third cavity, the second flow path comprising a barrier region having a top surface which is above the level of the first flow path. The device also comprises a wall member secured to at least a portion of the first face of the rigid body, the wall member disposed over the first cavity, the second cavity, and the third cavity, thereby defining a first chamber, a second chamber, and a third chamber. The third chamber has a width and a length, wherein the length is greater than the width. One or more inlet ports are in direct communication with at least the first chamber and the third chamber.

Preferably, the second flow path is in communication with the first flow path and first cavity only via the second cavity.

In one embodiment, the barrier region in the second flow path is disposed closer to the second chamber than to the third chamber along the second flow path.

In various embodiments, the one or more inlet ports can be is a single inlet port permitting access to both the first chamber and the third chamber; or the one or more inlet ports can comprise two separate ports, one positioned for access to the first chamber and a second positioned for access to the third chamber, or separate ports positioned for access to each of the first chamber, the second chamber, the third chamber and the second flow path.

In one embodiment, the first flow path is defined by an upper ledge and a lower ledge, the lower ledge creating the constricted region between the first cavity and the first flow path. Preferably, the top surface of the barrier region has a height higher than the upper ledge.

The device may further comprise a narrowing channel connecting the second flow path to the third chamber, the channel having its narrowest point adjacent the third chamber.

The device may comprise further chambers, such as a fourth chamber which is in fluid communication with the second flow path, at a point between the second and third chambers. In one embodiment, the fourth chamber is in fluid communication with the second flow path via an entry channel and a separate exit channel. The separate exit channel may have a narrowing profile, with its narrowest point adjacent the second flow path.

In a preferred embodiment, each of the first, second and third chambers contain a water-miscible liquid reagent. For example, the first chamber may contain a reagent capable of cell lysis, the second chamber an aqueous wash solution, and the third chamber an elution medium.

In a further preferred embodiment, the second flow path contains a water-immiscible fluid substance.

In one embodiment, the first flow path contains or is filled with the aqueous wash solution.

In a preferred embodiment, the first chamber further contains a plurality of solid carrier particles, which may comprise a plurality of magnetic particles. One or more of the particles in the plurality of magnetic particles is typically treated on its surface with an affinity reagent capable of associating with an analyte; the affinity reagent may be, for example, an antibody or antibody fragment with specific binding for an analyte, such as a protein, or a nucleic acid sequence capable of hybridizing with an analyte.

Also disclosed herein, in a related aspect, is a method for extracting an analyte from a sample. The method comprises providing a sample isolation device as disclosed herein; introducing a water-miscible liquid reagent into each of the first chamber, the second chamber, and the third chamber, wherein each chamber receives a different reagent, and wherein an amount of the reagent introduced into the second chamber is sufficient to fill the second chamber and the first flow path; introducing, if not already present in the first chamber, a plurality of solid phase carrier particles, such as described above, capable of associating with the analyte; introducing the sample into the first chamber; dispensing a water-immiscible substance into the second flow path, wherein the water-immiscible substance contacts the liquid reagent in the first flow path and the liquid reagent in the third chamber, forming first and second fluid interfaces, respectively; and transferring via an externally applied force, the plurality of solid phase carrier particles in the first chamber into the first flow path, into the second chamber, into the second flow path, and into the third chamber, whereby the transferring the plurality of solid phase carrier particles and any associated analyte, is effective to extract (isolate) the analyte from the sample.

Preferably each of the first and second interfaces remains essentially stationary during the transferring of the solid phase carrier particles. More generally, all water-miscible/water-immiscible fluid interfaces formed when the water-miscible and water-immiscible fluids are introduced and dispensed preferably remain essentially stationary during the transferring of the solid phase carrier particles.

In a preferred embodiment, the method further comprises dissociating the analyte from the carrier particles and removing liquid reagent containing the analyte from the third chamber.

In a further preferred embodiment, the first chamber contains a reagent capable of cell lysis, the second chamber contains an aqueous wash solution, and the third chamber contains an elution medium. The first flow path may contain or be filled with the aqueous wash solution.

In addition to the exemplary aspects and embodiments described above, further aspects and embodiments will become apparent by reference to the drawings and by study of the following descriptions.

Additional embodiments of the present devices and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1:
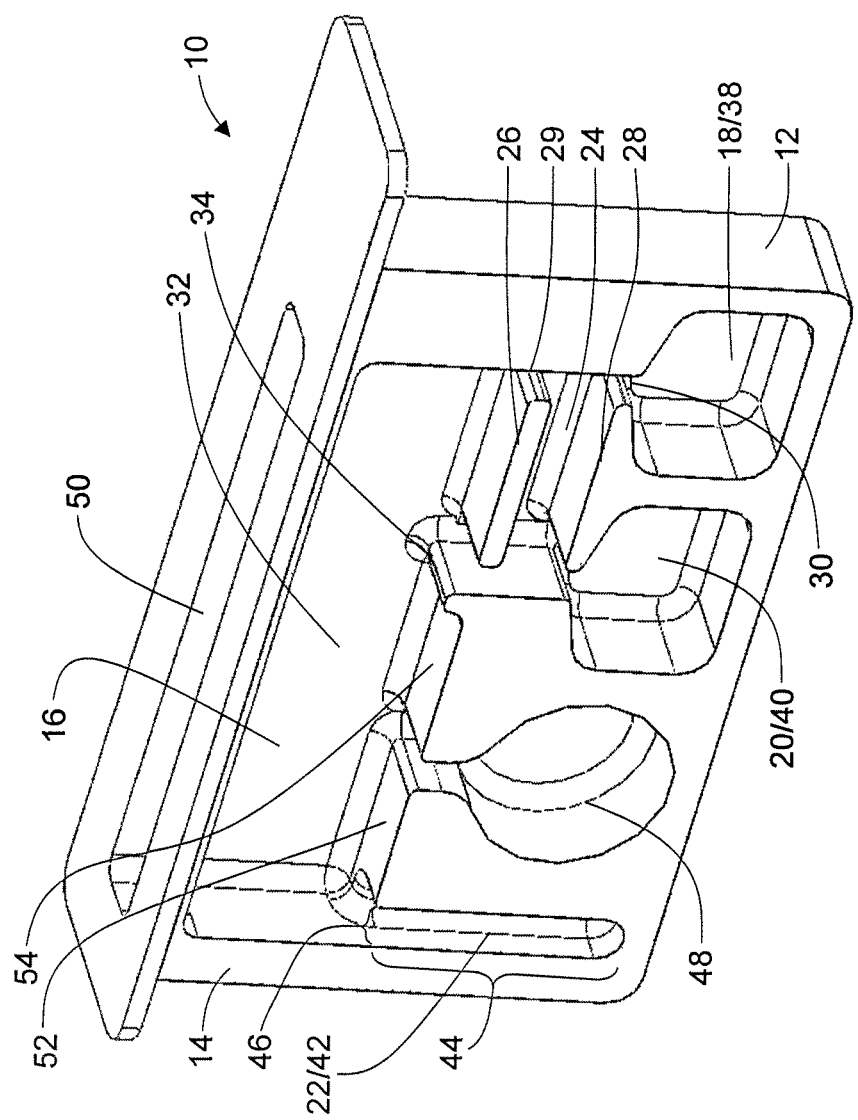
FIG. 1 shows one embodiment of a sample isolation device as disclosed herein.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

As used in this specification, the singular forms "a," "an," and "the" include plural referents unless the context clearly dictates otherwise.

A "liquid reagent", as the term is used herein, refers to any liquid contained within any of the chambers of the device as described herein, including aqueous, nonaqueous, and water-immiscible liquids.

A "reagent solution" typically refers to an aqueous solution. The "reagent" may be a chemical or biological substance that causes a chemical change to a sample component, or it may be simply a buffering agent, a salt, or a solvent.

As pertains to the present disclosure, a "biological sample" can include a tissue sample or a body fluid sample, which includes liquid, solid, and semisolid samples, e.g. blood, blood components such as plasma or serum, urine, saliva, sputum, mucous, amniotic fluid, semen, vaginal secretions, tears, spinal fluid, washings, feces, biopsy specimens, skin, nails, and hair.

A "specific binding member" or "affinity reagent", as used herein, is a molecule or moiety that specifically binds to a target analyte through chemical or physical means. Immunoreactive specific binding members include antigens or antigen fragments and antibodies or functional antibody fragments. Other specific binding pairs include biotin and avidin, carbohydrates and lectins, complementary nucleotide sequences, effector and receptor molecules, cofactors and enzymes, enzyme inhibitors and enzymes, and the like. In the extraction/isolation procedures described herein, a binding member is attached to a solid phase support, such as a plurality of paramagnetic particles, in order to extract the analyte from a sample containing non-target components. Following isolation of the particle-analyte complex from the non-target components, the complex is treated to effect removal of the analyte from the particles. Removal may be effected by, for example, heating the solution containing the complex and/or changing the chemical environment (e.g. salt concentration, pH, etc.). In other embodiments, a chemical or enzymatic reagent is used to disrupt the particle-analyte complex and thus effect removal of the analyte from the particles.

Particular examples of systems designed for formation of specific particle-analyte complexes and their subsequent release of analyte include, for example, the MagneHis™ protein purification system (Promega Corp., Madison, Wis.), in which paramagnetic precharged nickel particles (MagneHis™ Ni-Particles) are used to isolate polyhistidine- or HQ-tagged proteins from a sample matrix such as a cell lysate. Also preferred are functionalized solid supports as described in U.S. Pat. No. 7,354,750 (D. J. Simpson et al., Promega Corp.). Alternatively, the MagneGST™ protein purification system (Promega Corp.) employs immobilized glutathione paramagnetic particles (MagneGST™ Particles) to isolate glutathione-S-transferase (GST) fusion proteins. In the HaloTag® protein purification system (Promega Corp.), useful for purification of recombinant proteins, the protein of interest is expressed as a fusion protein, fused to a HaloTag® protein tag, which covalently binds to a HaloLink™ solid support via an immobilized chloroalkane ligand. Following separation of the fusion protein-resin complex from other matrix components, a specific protease then cleaves the target protein from the fused tag and the resin. The protease is also tagged such that it will remain bound to the resin.

An "isolated" analyte is one that has been separated from other constituents with which it is associated in a sample, such that it can be detected with a desired degree of accuracy and precision. The isolated analyte is typically dissolved in a solvent medium that may also contain non-interfering substances. In the case of a biological sample, the analyte is isolated from cellular constituents with which it is normally associated, and from other types of cells which may be present in the sample.

II. Sample Isolation Device

Disclosed herein, in one aspect, is a device useful for extraction of an analyte of interest from a matrix containing the analyte, such as a biological sample. The analyte could be, as described further below, a protein, a nucleic acid, or a cell or cell component. In other embodiments, the sample could be an environmental sample.

Isolation of an analyte using the device can be done manually or in an automated or semi-automated manner. For automated or semi-automated use, the device can be used in conjunction with an instrument such as described further below.

One embodiment of a device is shown in FIG. 1. As shown therein, a device 10 comprises a rigid body 12 having a first face 14 and a second face 16. The body 12 is molded or otherwise fabricated to define, at least, a first cavity 18, a second cavity 20, and a third cavity 22 within the first face. Preferably, the second face 16 is essentially solid.

A first flow path 24 connects first cavity 18 and second cavity 20. The first flow path is defined by an upper ledge 26 and a lower ledge 28. In one embodiment (not shown in FIG. 1), upper ledge 26 may be attached to or contiguous with wall 29. The area above upper ledge 26 may comprise a cavity, as shown in the figure, or it may be solid (thus forming an extension of wall 29).

In a preferred embodiment, one edge of lower ledge 28, together with wall 29, creates a constriction 30 in the first flow path, at the fluid flow path (inlet/outlet) into and out of the first cavity. The constriction region serves to reduce transfer or mixing of fluid between first cavity 18 and first flow path 24. The constriction region is preferably less than 10 mm, more preferably less than 5 mm, and may be 4 mm, 3 mm, 2 mm, or 1 mm or less in width. Preferably, the constriction region is at least 0.5 mm in width.

A second flow path 32 connects second cavity 20 and third cavity 22. The second flow path comprises a barrier region 34, having a height higher than a lower surface of upper ledge 26. The barrier region is preferably disposed closer to second cavity 20 than to third cavity 22 along the second flow path, and is more preferably adjacent the outlet of first flow path 24 nearest second cavity 20. The barrier serves to prevent liquid reagent in the first flow path 24 from entering the second flow path 32. As can be appreciated, the first flow path and the second flow path are contiguous, and define a single, continuous flow path through the device.

The device further comprises a wall member (not shown in FIG. 1 for purposes of clarity) that is secured to at least a portion of first face 14 of the rigid body. The wall member is disposed over at least the first cavity, the second cavity, and the third cavity, thereby defining a first chamber 38, a second chamber 40, and a third chamber 42. The wall member is also disposed over the flow paths.

The length (or depth) 44 of the third chamber, defined as the distance between the bottom of the chamber and the bottom surface of second flow path 32, is greater than its width 46. This permits easy and complete removal of the contents of the chamber, e.g. by insertion of a pipette into the chamber, to remove isolated analyte for further analysis and processing. The width of the chamber is sufficient to introduce a pipette or other extraction device into the chamber. The length is preferably at least 2 times, 3 times, 4 times, or 5 times greater than the width.

The device may include further chambers in addition to those described above, and in addition to those illustrated. For example, in selected embodiments, the device includes a fourth cavity and chamber, such as shown at 48, in fluid communication with second flow path 32.

The device of FIG. 1 also includes one or more inlet ports 50 in direct communication with at least the first chamber 38 and the third chamber 42. In some embodiments, such as that illustrated in FIG. 1, a single inlet port 50 permits access to both the first chamber and the third chamber. In other embodiments, the device comprises at least two separate ports, one positioned for access to the first chamber and a second positioned for access to the third chamber.

In preferred embodiments, the first chamber 38 contains a plurality of solid carrier particles (not shown in the figure). The device may be supplied with the particles, or they may be added to the first chamber prior to or during use. The solid carrier particles are able to pass through the chambers and flow paths upon application of an external force. In one embodiment, the particles are magnetic particles, and the external force is a magnetic force.

At least a plurality and preferably all of the particles comprise a surface affinity reagent, as defined above, which is effective to specifically and reversibly bind the target analyte; e.g. by specific antibody-antigen binding, by hybridization, by ionic or hydrogen bonding, or by other chemical interaction. The binding moiety may be, for example, a nucleic acid probe sequence, effective to hybridize to a target nucleic acid sequence, or an antibody or functional fragment thereof, effective to bind a target protein or other analyte. Any binding moiety of any desired specificity may be used.

In use or in preparation for use, each of the first, second and third chambers, and the fourth chamber, if present, contain a water-miscible liquid reagent. In preferred embodiments, the first chamber 38 contains a reagent capable of cell lysis; the second chamber 40 contains an aqueous wash solution; and the third chamber 42 contains an elution medium. The fourth chamber 48, if present, may contain a further wash solution, which may be an aqueous wash solution or an ethanolic wash solution.

The first flow path 24 contains or is filled with the water-miscible liquid reagent that is also present in second chamber 40. Preferably, it contains none or a minimal amount of the water-miscible liquid reagent that is present in first chamber 38.

In use or in preparation for use, the second flow path 32 in the device contains a water-immiscible fluid substance. The water-immiscible fluid substance forms a continuous layer within the second flow path 32, including any cavity region over top ledge 26. The continuous layer of water-immiscible fluid substance may have an interface with a water-miscible liquid reagent(s) starting at or below the level of the top surface of barrier 34. Preferably, however, it is in contact with barrier 34 as well as surfaces 52 and 54. The water-immiscible fluid may substantially fill the entire second flow path, up to approximately the level of port 50, or it may only partially fill the flow path, as long as a sufficiently deep continuous layer is present to allow passage of the plurality of particles through the fluid, in a manner to be described below.

Figure 2:
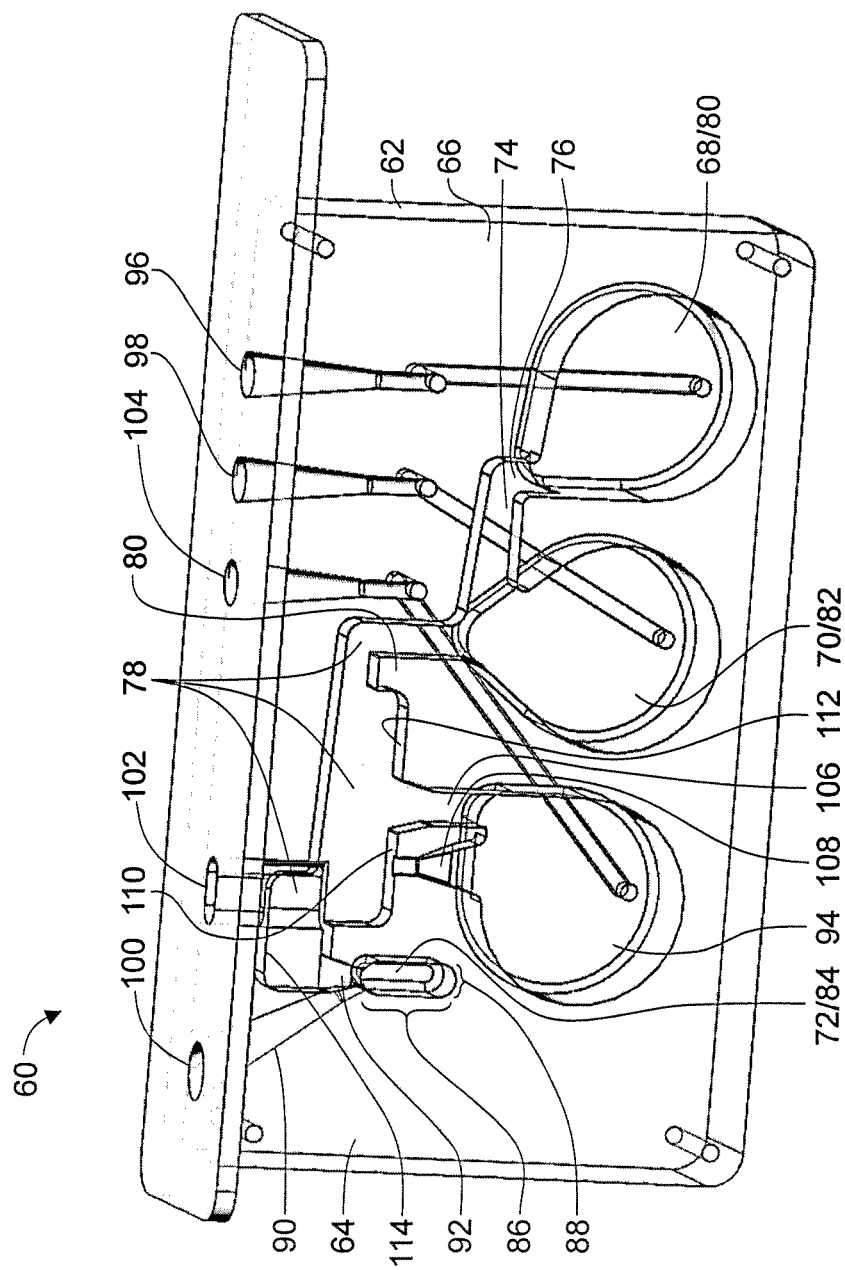
FIG. 2 shows a further embodiment of a sample isolation device as disclosed herein.

A second embodiment of the device is shown in FIG. 2. As for the device of FIG. 1, the device 60 of FIG. 2 comprises a rigid body 62 having a first face 64 and a second face 66. The body 62 is molded or otherwise fabricated to define, at least, a first cavity 68, a second cavity 70, and a third cavity 72 within the first face. Preferably, the second face 66 is essentially solid. The device further comprises a wall member (not shown) over the cavities and flow paths within the first face 64.

A first flow path 74 connects the first cavity 68 and the second cavity 70. In a preferred embodiment, flow path 74 includes a constriction 76 at the outlet of the first cavity. The constriction region serves to reduce transfer or mixing of fluid between the first cavity 68 and the first flow path 74. The constriction region is preferably less than 10 mm, more preferably less than 5 mm, and may be 4 mm, 3 mm, 2 mm, or 1 mm or less in width. Preferably, the constriction region is at least 0.5 mm in width.

A second flow path 78 connects the second cavity 70 and the third cavity 72. The second flow path may comprise a barrier region 80 along its lower surface. The barrier region is preferably disposed closer to the second cavity 70 than to the third cavity 72 along the second flow path. The barrier aids in preventing liquid reagent in the first flow path 74 from entering the second flow path 78.

The device further comprises a wall member (not shown in the figure for purposes of clarity) that is secured to at least a portion of the first face 64 of the rigid body. The wall member is disposed over at least the first cavity, the second cavity, and the third cavity, thereby defining a first chamber 80, a second chamber 82, and a third chamber 84. The wall member is also disposed over the flow paths.

The length (or depth) 86 of the third chamber is greater than its width 88. This permits easy and complete removal of the contents of the chamber, e.g. by insertion of a pipette into the chamber, to remove isolated analyte for further analysis and processing. The width of the chamber is sufficient to introduce a pipette or other extraction device into the chamber. The length is preferably at least 2 times, 3 times, 4 times, or 5 times greater than the width.

A conduit 90 may be provided for insertion of a pipette or similar device for removal of the solution of isolated analyte from chamber 84. The conduit is constructed such that the removal device contacts the aqueous solution of isolated analyte but does not contact oil (or other water-immiscible fluid) in channel 92 above the chamber.

The device may include further chambers in addition to those described above, and in addition to those illustrated. For example, in selected embodiments, the device includes a fourth cavity and chamber, such as shown at 94, in fluid communication with second flow path 78.

The device of FIG. 2 also includes inlet ports 96, 98, 100, 102, and (preferably) 104, each in direct communication, as shown in FIG. 2, with, respectively, the first, second, and third chambers, flow path 78, and fourth chamber 94 if present.

As noted above, chamber 94, when present, is in fluid communication with second flow path 78, via inlet channel 106. Preferably, a separate outlet channel 108 is also provided, as shown in FIG. 2. The outlet channel may be constructed such that it is tapered, e.g., its upper end is narrower than its lower end (adjacent chamber 94), in width, in depth, or in both dimensions, as illustrated.

In a similar manner, channel 92 connecting chamber 84 to the adjacent portion of flow path 78, is also preferably constructed such that its upper end is narrower than its lower end (adjacent chamber 84), in width, in depth, or in both dimensions, as illustrated. The lower end of channel 92 is preferably no wider than is required to insert a pipette or similar device into chamber 84 for removal of isolated sample.

In preferred embodiments, the first chamber 80 contains a plurality of solid carrier particles (not shown in the figure). The device may be supplied with the particles, or they may be added to the first chamber prior to or during use. The solid carrier particles are able to pass through the chambers and flow paths upon application of an external force. In one embodiment, the particles are magnetic particles, and the external force is a magnetic force.

At least a plurality and preferably all of the particles comprise a surface affinity reagent, as defined above, which is effective to specifically and reversibly bind the target analyte; e.g. by specific antibody-antigen binding, by hybridization, by ionic or hydrogen bonding, or by other chemical interaction. The binding moiety may be, for example, a nucleic acid probe sequence, effective to hybridize to a target nucleic acid sequence, or an antibody or functional fragment thereof, effective to bind a target protein or other analyte. Any binding moiety of any desired specificity may be used.

In use or in preparation for use, each of the first, second and third chambers, and the fourth chamber, if present, contains a water-miscible liquid reagent. In preferred embodiments, the first chamber contains a reagent capable of cell lysis; the second chamber contains an aqueous wash solution; and the third chamber contains an elution medium. The fourth chamber, if present, may contain a further wash solution, which may be an aqueous wash solution or an ethanolic wash solution.

The first flow path contains or is filled with the water-miscible liquid reagent that is also present in second chamber. Preferably, it contains none or a minimal amount of the water-miscible liquid reagent that is present in first chamber.

In use or in preparation for use, the second flow path in the device contains a water-immiscible fluid substance. The water-immiscible fluid substance forms a continuous layer within the second flow path, preferably including the region over the second chamber (82) and flow path (74). The continuous layer of water-immiscible fluid substance preferably has an interface with a water-miscible liquid reagent(s) that is below the level of the top surface of the barrier (80). Preferably, water-immiscible fluid substance is also in contact with the lower edge of the fluid flow path above the second chamber, indicated as surfaces 110 and 112. The water-immiscible fluid may substantially fill the entire second flow path, up to the level of a upper ledge of the device, such as ledge 114, or it may only partially fill the flow path, as long as a sufficiently deep continuous layer is present to allow passage of the plurality of particles through the fluid, in a manner to be described below.

Features of the device of FIG. 2, such as, for example, narrowed channels 108 and/or 92 and multiple access ports 96, 98, 100, 102 and 104, may also be incorporated into the device of FIG. 1, and vice versa. In general, unless otherwise indicated, reference herein to "the device" includes the device of FIG. 1, the device of FIG. 2, and any device falling within the scope of the more general disclosure herein.

Figure 3A:
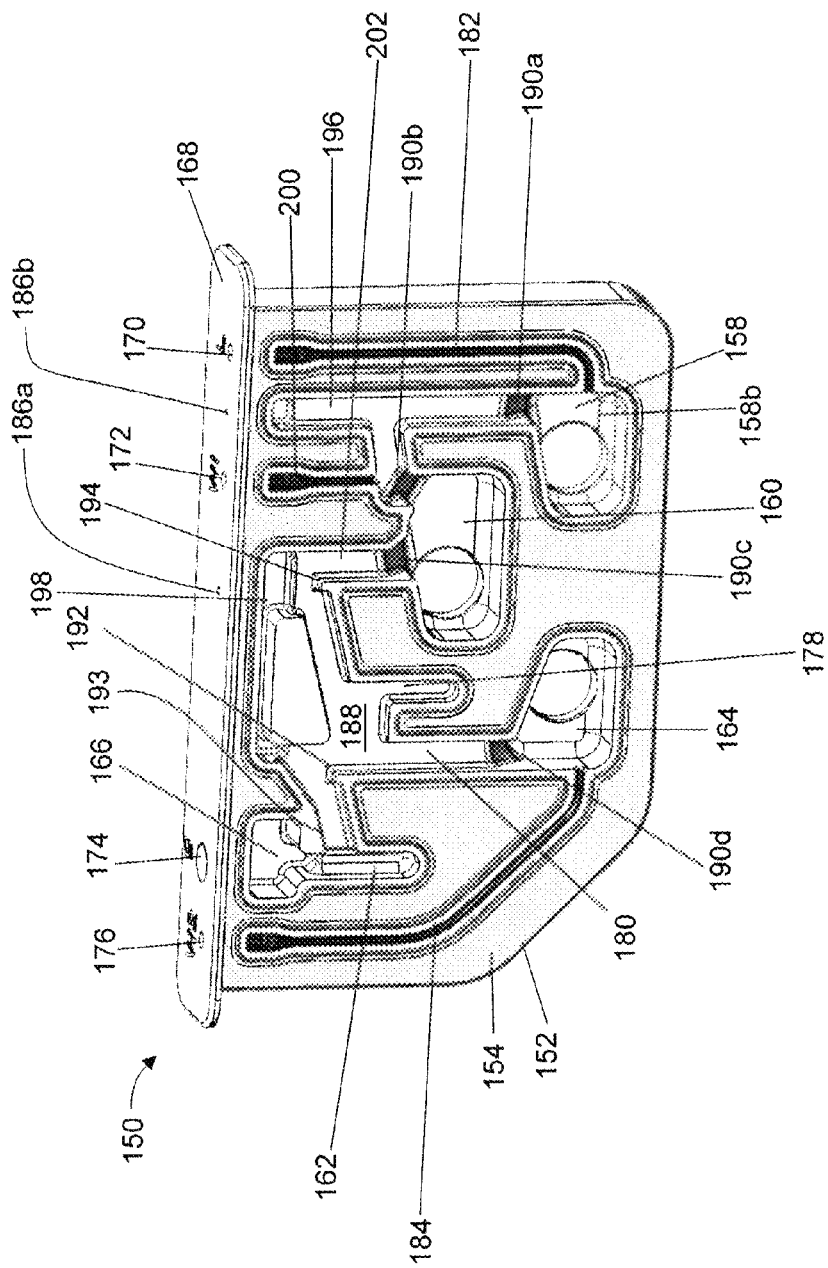
FIGS. 3A-3B show a front view (FIG. 3A) and a back view (FIG. 3B) of another embodiment of a sample isolation device.
Figure 3B:
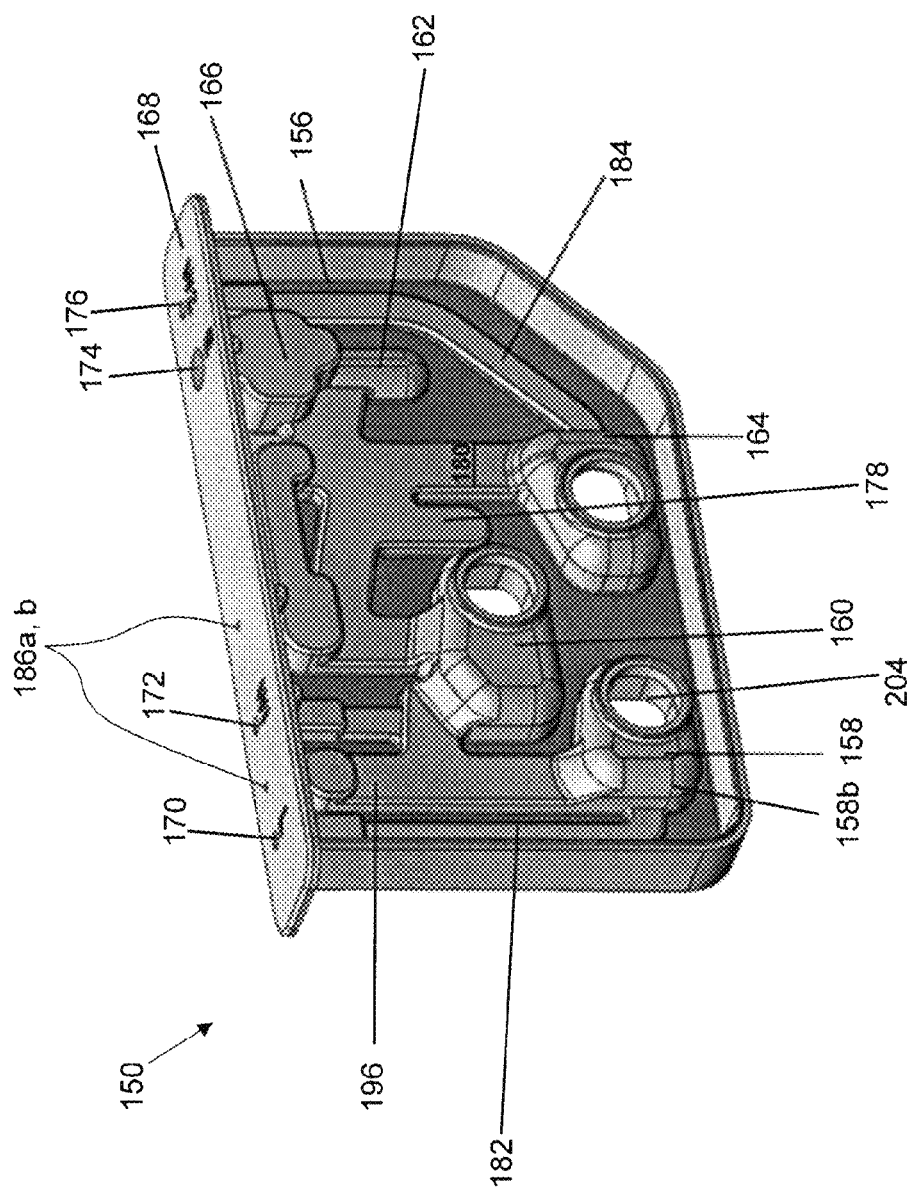

Another embodiment of a device is shown in FIGS. 3A-3B. Device 150 is comprised of a planar, rigid body 152 having a front side 154 and a back side 156. Not shown in the drawing are a front wall member and a back wall member that are present when the device is provided for use. It will be appreciated that when the wall members are present, the cavities and conduits in the rigid body are enclosed chambers and channels that can contain a liquid.

Device 150 comprises a plurality of chambers, denoted in FIG. 3A as chambers 158, 160 and 162. The device may optionally include additional chambers, such as optional chambers 164 and 166. Each chamber in the device is accessible to the external environment or a user by a port. In one embodiment, the ports are positioned along a common edge of the device. As seen in FIG. 3A-3B, an upper edge 168 of the device comprises one or more ports for access to the chambers. The embodiment shown includes a first port 170 for access to a first chamber 158, a second port 172 for access to a second chamber 160, and a third port 174 for access to a third chamber 162. If optional chamber 164 is present, the device includes an optional fourth port 176 for access to optional chamber 164. In one embodiment, the number of ports of entry to the device is equal to the number of reaction or processing chambers in the device, as this provides a dedicated entry port to each processing chamber to prevent cross-contamination of the fluid to be introduced into each chamber. In this regard, a reaction or processing chamber of the device is distinguished from chambers in the device for a purpose other than receiving a liquid and the solid carrier particle/analyte complexes for extraction and isolation of an analyte from the sample. For example, device 150 includes an elongate chamber 178 that is positioned to receive overfill liquid of chamber 164, to ensure that chamber 164 and channel 180 in the fluid flow path between processing chambers is filled with the desired liquid.

Each port and associated chamber are connected by a conduit. In one embodiment, at least one port and associated chamber are in communication by an elongated conduit positioned so that a liquid introduced via the port enters a bottom portion of its associated chamber. This feature is seen in device 150 with regard to chamber 158 and its associated port 170. Chamber 158 and port 170 are connected by elongated conduit 182 that extends from the port to an opening at the lower portion 158b of chamber 158. Lower portion intends the lower half of the chamber relative to a horizontal plane that intersects the center of the chamber. Chamber 164 and port 176 are in fluidic communication by elongated conduit 184 that extends from the port to an opening in the lower portion of chamber 164. As can be appreciated, the position of the conduit opening into the lower portion of a chamber allows for air in the chamber to be displaced upward as liquid enters the chamber, allowing the chamber to fill completely with liquid with minimal trapped air. In the regard, device 150 may include air vents, such as vents 186a and 186b. The air vents are in fluid communication with a flow path and/or a chamber of the device, to permit air to exit the chamber, conduit and/or device as a liquid is introduced into a chamber and/or flow path of the device.

Device 150 comprises a fluid flow path 188 that extends from first chamber 158 into the second chamber 160 into optional chamber 164 and into chamber 162. Fluid flow path 188 for purposes of discussion is separated into a first fluid flow path, that extends from the exit of first chamber 158 to the exit of the second chamber 160, and a second flow path that extends from the exit of the second chamber to the final processing chamber in the device (chamber 162 in the device of FIG. 3A). The conduits that form fluid flow path 188 include features for fluid control, now to be described. In one embodiment, the fluid flow path includes one or more constrictions, indicated in device 150 at 190a, 190b, 190c and 190d. The constrictions are narrowing in the channel/conduit of the fluid flow path, and are large enough for solid carrier particles complexed with an analyte to pass individually or collectively, yet are more narrow than the channel/conduit. The constrictions are preferably positioned in the fluid flow path entry into and exit from a processing chamber, and assist in reducing undesired carry-over of liquid (i.e., cross-contamination) from a chamber into the flow path and into adjacent chambers. As seen, the first flow path connects the first and second chambers, and includes a constriction region 190a. This embodiment additionally includes constriction region 190 in the first fluid flow path.

The conduits/channels of the fluid flow path may also include barriers that control fluid flow. In Device 150 barriers are positioned in fluid flow path between the final processing chamber 162 and the upstream processing chambers 160, 164. These barriers are indicated in FIG. 3A at 192 and 194. The barrier positioned along the edge of the channel prevents fluid from creeping by capillary action along the channel edge causing some fluid to undesirably enter a conduit or chamber where it is not intended to be. The second fluid flow path connects the second cavity and a third cavity, and includes a barrier region 194, as well as a second barrier 192.

Another feature in device 150 is an optional angled wall, such as wall 193 disposed in the conduit at the entry/exit to chamber 162. An angled wall at one or more locations in the device serves to direct and fluid flow and bubble movement into, for example, overflow chambers or into air vents. Another feature in device 150 is the relative volume of the first and second flow paths, where the second flow path 188 is larger in volume than the first flow path between chamber 158 and chamber 160. The larger volume in one flow path relative to a second flow path provides fluid control, and an increased tolerance to required precision in the volume control for certain chambers in the device. In addition, one or more overflow chambers, such as chamber 178, can be included in the device to provide fluid and volume control.

Device 150 may also include one or more overflow regions, such as region 178. The device may also include spaces that are not intended to be filled with a liquid and are designed as regions for air to flow and entrapped bubbles to collect as they are released from the liquid. For example, space 196 above the first chamber and space 198 above the second and optional chambers are vertically above the fluid flow path, and provide regions that remain unfilled with liquid during use for receiving entrapped air.

Chamber 162 is the device is a final processing chamber, and may contain an elution medium for release of the isolated analyte from the solid carrier particles. The position of chamber 162 and the shape of chamber 162 are design features that enhance performance and functionality of the device. In use, a liquid is introduced into each of the processing chambers. In device 150, a user is instructed to first fill chamber 160 with a wash solution (which can be a buffer, a salt solution, a water-alcohol solution, etc). Chamber 160 is filled via port 172 and conduit 200 with a volume of solution greater than the chamber's capacity and until the wash solution just slightly overflows into the upstream chamber, first chamber 158. As can be appreciated, the conduit between the first chamber and wash chamber 160 is placed so that when the wash chamber is filled excess fluid flows into the upstream chamber (first chamber 158), rather than into downstream chambers.

Once the wash chamber 160 and conduit between the wash chamber and the chamber upstream, chamber 158, are filled with wash solution, the adjacent upstream chamber, first chamber 158, may be filled with a liquid reagent. In one embodiment, the liquid reagent in first chamber 158 is one that lyses cells in a sample that is placed in the first chamber. A plurality of solid carrier particles is present in, or may be introduced into, the first chamber before, concurrent with, or after placement of the sample in the chamber. The lysis reagent may be present in the chamber in dried form, and a buffer to solubilize the dried reagent is introduced by port 170 and conduit 182 into the chamber. The sample and/or solid carrier particles are also introduced via port 170 into chamber 158. The solid carrier particles are capable of associating with an analyte to be detected, either by a surface coating for a specific binding interaction with the analyte or by a non-covalent, non-specific interaction (like hydrogen bonding or van der walls forces).

Liquid is introduced into first chamber 158 in a volume sufficient to fill the chamber and the conduit downstream of the chamber, to form an interface of lysis liquid reagent and wash solution in the fluid flow path.

A liquid is then introduced into the final processing chamber, chamber 162, and if present, into the optional chamber 164. In the final processing chamber the analyte of interest is isolated from the sample, and present in the final processing chamber is only the analyte of interest complexed with a solid carrier particle. In embodiments where the analyte of interest is a nucleic acid or protein, it is desired that no liquid reagents from the upstream chambers be carried into or inadvertently be introduced into the final processing chamber, as the reagents in the upstream processing chambers can interfere with detection or amplification of the isolated analyte of interest. Accordingly, the shape and position of the final processing chamber in the device is such to minimize the risk of contamination from liquids in upstream chambers. As seen in FIG. 3A, the final processing chamber 162 is situation vertically above the upstream chambers, so that gravity will assist in preventing fluid from the upstream chambers from flowing into the final processing chamber 162.

After the chambers in the device are filled with their respective liquid reagents, a water-immiscible liquid is introduced via port 174 into the fluid flow path 188. The water-immiscible liquid preferably fills the flow path 188 that extends from the elution chamber (thus defining an interface of liquid the final processing chamber 162 and water-immiscible liquid at the point where the flow path terminates into chamber 162), to the conduit above the wash chambers 164 and 160. There is, therefore, an interface of wash liquid and water-immiscible liquid at the junction where these fluids meet in conduit 180 and in conduit 202. The feature of introducing the water-immiscible liquid via the port into the final processing chamber is a further design feature to minimize the risk of contamination from liquids in upstream chambers inadvertently entering the final processing chamber.

The dimensions of the channels in the fluid flow path are sufficiently large so that fluid when introduced into a channel does not move by capillary action, and are small enough so that turbulence does not occur when fluid is introduced, to prevent mixing and emulsion formation.

With reference to FIG. 3B, the device may also include a localized thin wall region in one or more of the processing chambers, such as region 204 in chamber 158. The molded body shown in the drawings if formed with a hole or gap region 204, that can be covered with a thin wall member which is secured by a suitable means to the back side of the molded body. The thin wall region in a chamber provides a place where a sonication probe can be applied, to give localized mixing in the chamber, if desired. The localized nature of the thin wall region isolates the mixing to the associated chamber, since, as can be appreciated, application of sonic energy to a contiguous wall member can result in transfer of the energy through the entire wall member causing undesired mixing in conduits, and at the interfaces of solution/water-immiscible liquid. Mixing at these interfaces is especially undesired, as emulsions form, and the defined interface with its benefits of extracting an analyte of interest from a sample is lost.

Features of the device of FIG. 3 may also be incorporated into the device of FIG. 1, the device of FIG. 2, and vice versa. In general, unless otherwise indicated, reference herein to "the device" includes the device of FIG. 1, the device of FIG. 2, and the device of FIG. 3, and any device falling within the scope of the more general disclosure herein.

In the device embodiments described herein, the solid carrier particles preferably remain in contact with a liquid throughout their movement through the device. However, in one embodiment, an air passage or chamber may be included for air drying of the particles, particularly subsequent to any exposure to lower alcohols such as ethanol.

Mixing members may be included in any of the chambers. The mixing member(s) may comprise stir bar(s) or mixing ball(s), which can be magnetically activated from outside of the device. Alternatively, the mixing member(s) may comprise one or more series of raised ridges ("washboards") in one or more cavity walls and/or within one or more flow paths of the rigid body. Preferably, these ridges are arranged within the cavities and/or flow paths and have a dimension such that each particle must pass over the ridges in being transported through the cavities and/or flow paths, in a manner to be described below.

The assembled device can be designed for automated or semi-automated use within an instrument that may hold one or a plurality of such devices, as described further below. Accordingly, the device may contain external features, such as notches or ridges, used to properly align the device within the instrument.

III. Methods of Use

In using the device described herein for isolation of a target substance from a sample, such as a biological sample, water-miscible liquid reagents are introduced into each of the first chamber, the second chamber, and the third chamber, where each chamber preferably receives a different reagent. In one embodiment, the first chamber receives a liquid reagent capable of cell lysis, and the second chamber receives an aqueous wash solution. The amount of the reagent, e.g. the wash solution, introduced into the second chamber is sufficient to fill the second chamber and the first flow path; that is, in the device of FIG. 1, the area between the upper and lower ledges 26 and 28.

Preferably, the third chamber receives an elution medium, as described further below. The fourth chamber, if present, may receive a further wash solution, which may be an aqueous wash solution or an ethanolic wash solution.

A plurality of solid phase carrier particles, such as described above, is introduced into the first chamber, or they may be present prior to addition of the reagent solutions. The solid carrier particles, as described above, are able to pass through the chambers and flow paths upon application of an external force. In one embodiment, the particles are magnetic particles, and the external force is a magnetic force. At least a plurality, and preferably all, of the particles comprise a surface affinity reagent, as described above, which is effective to specifically and reversibly bind a target analyte.

A sample is introduced into the first chamber, which preferably contains a lysis reagent, as noted above, effective to lyse cells in a biological sample and release any target analyte into the aqueous medium. Depending on the nature of the sample, it may be pretreated in various ways, e.g. by dilution with a standard buffer, if necessary.

After addition of the sample and binding particles (which may be added in either order), a water-immiscible fluid is introduced into the second flow path (32, 78), such that it contacts the water-miscible liquid reagents in the third chamber, in the fourth chamber if present, and in the portion(s) of the first flow path flanking upper ledge (26 in FIG. 1). The introduction of the water-immiscible fluid thereby forms a plurality of water-miscible/water-immiscible interfaces, i.e. a first interface with the reagent solution in the second chamber (40, 82, 162), a second interface with the reagent solution in the third chamber (42, 84, 162), and further interface(s) with the reagent in the fourth chamber (48, 94, 162), if present. Preferably, all of the water-miscible/water-immiscible fluid interfaces, formed when the fluids are dispensed into the chambers and channels in accordance with the disclosed method, remain essentially stationary when the solid carrier particles are moved through the device, in a manner to be described below. In essence, these fluid interfaces preferably remain fully stationary, with the exception of minor disturbances that may be caused by the movement of the particles themselves through the interfaces.

The water-immiscible fluid substance thus forms a continuous layer within the flow path (32, 78, 188) and the region over upper ledge (26, in the device of FIG. 1), and is preferably in contact with the entire top surface of barrier (34, 80, 194) as well as the lower surfaces of the flow path (52, 110, 192 and 54, 112). More preferably, the water-immiscible fluid substance fills the narrowed region of channels 108 and/or 92 (in the embodiment of FIG. 2; 190*d*, 190*c* in embodiment of FIG. 3) as well. Preferably, the water-immiscible substance does not fill, and more preferably it does not enter, the first flow path (24, 74, upstream portion of 188) between the first (lysis) chamber (38, 80, 158) and the second (wash) chamber (40, 82, 160).

Prior to or subsequent to introduction of the water-immiscible fluid as described above, the sample is admixed with lysis buffer and affinity-treated particles in first chamber 38, for a sufficient time, at a sufficient temperature, and with sufficient agitation to lyse cells and allow the target analyte, such as a nucleic acid or protein, to bind to the treated particles. The external sides of the device corresponding to first chamber (38, 80, 158) are accessible to a heat source if required, and mixing elements such as stir bars, stir particles, or "washboard" surfaces are preferably provided within the chamber. Mixing may also be facilitated by moving the particles within the chamber by the above-referenced externally applied force.

The particle-bound analyte is then exposed to the various liquid reagents within the device by a process in which the particles are moved, by virtue of an externally applied force, though the chambers and flow paths. Thus, following the disposition of fluids into the respective chambers and flow paths, there is preferably minimal transport of fluid within the device.

Preferably, the particles are paramagnetic particles, such that they can be moved through the chambers and flow paths via an externally applied magnetic force. However, other means of moving the particles via an externally applied force can be used, including air pressure, vacuum, centrifugal force, or electrical fields for charged molecules or particles.

Following cell lysis and binding of analyte, if present, to the affinity-treated particles, the particles are transferred, via the externally applied force, from the first chamber (38, 80, 158) into the first flow path (24, 74, upstream portion of 188), then into the second chamber (40, 82, 160), and then into the water-immiscible fluid in the second flow path (32, 78, most downstream portion of 188).

Upon entering the second chamber (40, 82, 160), the solution therein and/or the particles may be further agitated, using one or more agitation strategies as described for the first chamber.

The particles are then moved into the layer of water-immiscible fluid present in the flow path (32, 78, 188). As described in U.S. Patent Application Publication No. 2009/0246782, which is incorporated herein by reference, movement of the carrier particles into the water-immiscible fluid, such as a lipophilic fluid or a polar, hydrophobic fluid, serves to further isolate the particle-bound analyte from remaining components of the sample, which tend to remain in the aqueous phase.

As described above, the outlet of first chamber (38, 80, 158) into the first flow path (24, 74) preferably contains a constriction (30, 76, 190*a*), which minimizes transfer of fluid from the first chamber to the second chamber. Accordingly, minimal fluid from the first chamber (lysis reagent) enters the first flow path, even less enters the second chamber, and virtually none contacts the second flow path (32, 78, most downstream portion of 188), which contains the water-immiscible fluid.

As noted above, all of the water-miscible/water-immiscible fluid interfaces, formed when the fluids are dispensed into the chambers and channels in accordance with the disclosed method, preferably remain essentially stationary when the solid carrier particles are moved through the device.

The design of the sample isolation device as disclosed herein presents various advantages, including the following. It has been found that, when the particles containing bound analyte freshly extracted from the lysis mixture in chamber (38, 80, 158) are washed in wash chamber (40, 82, 160) prior to being introduced to the water-immiscible fluid in the flow path (32, 78, 188), there is less tendency for the particles to clump and/or to stick to the walls of the chamber(s) and flow path(s), as compared to when particles containing bound analyte freshly extracted from the lysis mixture in chamber (38, 80, 158) are directly introduced to the water-immiscible fluid.

The "water-immiscible fluid" is a liquid or semisolid fluid that phase separates when diluted with an equal part of water; preferably, the fluid phase separates when diluted 2:1, 4:1, or 10:1 with water. More preferably, the water-immiscible fluid is substantially fully immiscible with water; it is preferably immiscible with lower alcohols as well. Examples of suitable water-immiscible fluids include lipophilic fluids such as waxes, preferably liquid waxes such as Chill-Out™ 14 wax (MJ Research), and oils, such as mineral oil, paraffin oil, or silicone, fluorosilicone, or fluorocarbon oils. Semisolid waxes may also be used, as long as the external force applied is sufficient to move the solid phase carrier through the medium; heat may be applied to reduce viscosity. In general, however, waxes and oils that are liquid at room temperature are preferred. Also suitable are, for example, hydrocarbon solvents such as toluene, hexane, or octane, and polar hydrophobic solvents such as 1,4-dioxane, acetonitrile, tert-butanol or higher (up to about C12) alcohols or acetates, cyclohexanone, or t-butyl methyl ether. (If a polar hydrophilic solvent is employed, the water-miscible liquid reagents employed in the device preferably do not include substantial amounts of lower alcohols.) Preferably, the water-immiscible fluid has a low vapor pressure and a specific gravity less than that of water. In selected embodiments, the water-immiscible fluid is an oil such as mineral oil.

The particles may then be moved into fourth chamber (48, 94, 164) (second wash chamber), which, in some embodiments, contains a water/alcohol solution, such as aqueous ethanol. In alternative embodiments, particularly in situations where traces of alcohol in the final analyte solution are to be avoided, chamber (48, 94, 164) may be absent, or it may be bypassed.

In one embodiment, the second wash chamber (48, 94, 164), when present, has a separate exit channel (e.g., 68 in FIG. 2), to avoid contact of the beads with residue from the first wash chamber that may be present in entry channel (66, 106).

In one embodiment, an air passage or chamber may be included for air drying of the particles, particularly subsequent to any exposure to lower alcohols such as ethanol.

The particles are then moved through the water-immiscible fluid in flow path (32, 78, 188) through a channel (e.g. 92 in FIG. 2) and into elution chamber (third chamber) (42, 84, 162), where the bound isolated analyte is removed from the particles. In some cases, heat may be applied; e.g. to release hybridized nucleic acids from a probe attached to the particles. Other reagents, such as linkage cleaving reagents, including enzymes, may be included in or added to the elution buffer as needed to facilitate release of the bound analyte from the particles.

Finally, a solution of elution buffer and eluted and isolated analyte, if present, is removed from the elution chamber. In the embodiment shown in FIG. 2, the narrowing of the channel 92 serves to minimize the area of the interface between the water-immiscible fluid (e.g. oil) and the aqueous solution present in the wash chamber (94). Similarly, the narrowing of the channels at constrictions 190c and 190d in the device of FIG. 3A minimizes the area of the interface between the water-immiscible fluid (e.g. oil) and the aqueous solution present in the wash chamber (164) This feature serves to minimize the amount of the water-immiscible fluid that may be pushed down into the aqueous solution when a pipette is inserted to remove the solution. During removal of the solution, the released particles are preferably segregated from the solution, e.g. by continued application of magnetic force for magnetic particles.

IV. Automated System

As noted above, the device can be used in a semi-automated or automated manner, in conjunction with an instrument that may hold one or a plurality of such devices. For example, the device is inserted into the instrument after loading of the sample, and fluids are dispensed into the various compartments and flow paths as described above, in the appropriate order, in automated fashion. The particles can then be moved through the device by an externally applied force, preferably a magnetic force, also in automated fashion. Removal of the sample may also be automated. Alternatively, the process is semi-automated, such that one or more of these procedures is done manually while one or more others is done automatically.

In one embodiment, a mechanical stage within the instrument is used to move the sample isolation device(s) to and from e.g. reagent dispensing stations, magnetic bead movers, and/or heating elements, as needed. In one exemplary design, the instrument includes a cartridge loading and unloading station, with the capacity for several cartridges, and a sample preparation station, which includes stations dedicated to liquid dispensing, mixing, particle moving, and heating.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A device, comprising:
a rigid body having a first face and a second face, and defining within said first face:
a first cavity having an outlet, a second cavity, and a third cavity,
a first flow path positioned between and connecting the outlet of the first cavity and the second cavity,
said outlet comprising a constricted region between said first cavity and said first flow path, wherein the outlet constricted region is more narrow than the first flow path, and
a second flow path positioned between and connecting the second cavity and the third cavity, the second flow path comprising an upper and a lower surface and a barrier region having a top surface which is above the level of the lower surface of the second flow path;
wherein the first flow path is contiguous with the second flow path;
a wall member secured to at least a portion of the first face of the rigid body, said wall member disposed over the first cavity, the second cavity, and the third cavity, thereby defining a first chamber, a second chamber, and a third chamber, the third chamber having a width and a length, wherein the length is greater than the width; and
one or more inlet ports in direct communication with at least the first chamber and the third chamber for introduction of one or more water-miscible liquid reagents into each of the first and third chambers.

2. The device of claim 1, wherein said second flow path is in communication with said first flow path and first cavity only via said second cavity.

3. The device of claim 1, wherein said barrier region in said second flow path is disposed closer to the second chamber than to the third chamber along the second flow path.

4. The device of claim 1, wherein the one or more inlet ports comprise two separate ports, one positioned for access to the first chamber and a second positioned for access to the third chamber.

5. The device of claim 1, wherein the first flow path is defined by an upper ledge and a lower ledge, said lower ledge creating said constricted region between said first cavity and said first flow path.

6. The device of claim 1, further comprising a narrowing channel connecting said second flow path to said third chamber, said channel having its narrowest point adjacent said third chamber.

7. The device of claim 1, wherein each of the first, second and third chambers contains a water-miscible liquid reagent.

8. The device of claim 7, wherein the first chamber contains a reagent capable of cell lysis, the second chamber contains an aqueous wash solution, and the third chamber contains an elution medium.

9. The device of claim 8, wherein said second flow path contains a water-immiscible fluid substance.

10. The device of claim 8, wherein the first flow path contains or is filled with said aqueous wash solution.

11. The device of claim 1, wherein the first chamber further contains a plurality of solid carrier particles.

12. A method for extracting an analyte from a sample, comprising:
providing a device according to claim 1,
introducing a water-miscible liquid reagent into each of the first chamber, the second chamber, and the third chamber, wherein each chamber receives a different reagent, and wherein an amount of the reagent introduced into the second chamber is sufficient to fill the second chamber and the first flow path;
introducing, if not already present in the first chamber, a plurality of solid phase carrier particles capable of associating with said analyte;
introducing said sample into the first chamber;
dispensing a water-immiscible substance into the second flow path, wherein the water-immiscible substance contacts the liquid reagent in the first flow path and the liquid reagent in the third chamber, forming first and second fluid interfaces, respectively; and
transferring via an externally applied force, the plurality of solid phase carrier particles in the first chamber into the first flow path, into the second chamber, into the second flow path, and into the third chamber, whereby said moving transfers the solid phase carrier particles and any associated analyte, thereby extracting the analyte from the sample.

13. The method of claim 12, wherein said first and second interfaces remain essentially stationary during said transferring of said solid phase carrier particles.

14. The method of claim 12, wherein water-miscible/water-immiscible fluid interfaces formed when said water-miscible and water-immiscible fluids are introduced and dispensed remain essentially stationary during said transferring of said solid phase carrier particles.

15. The method of claim 12, wherein the first chamber contains a reagent capable of cell lysis, the second chamber contains an aqueous wash solution, and the third chamber contains an elution medium.

* * * * *